United States Patent [19]

Varsanyi et al.

[11] 4,242,333
[45] Dec. 30, 1980

[54] NEMATOCIDAL UNSUBSTITUTED PHENYL ESTERS OF O-ALKYL-S-ALKYL-THIOPHOSPHORIC ACID

[75] Inventors: Denis Varsanyi, Arlesheim; Gert Handschin, Reinach, both of Switzerland

[73] Assignee: Vseoyuznii Na'uchno-Isledova Telskii Gustitut Khimichesti Institute, U.S.S.R.

[21] Appl. No.: 888,942

[22] Filed: Mar. 22, 1978

Related U.S. Application Data

[60] Continuation of Ser. No. 746,689, Dec. 2, 1976, abandoned, which is a continuation of Ser. No. 652.865, Jan. 27, 1976, abandoned, which is a division of Ser. No. 445,011, Feb. 22, 1974, abandoned, which is a continuation of Ser. No. 273,075, Jul. 19, 1972, abandoned.

[30] Foreign Application Priority Data

Jul. 23, 1971 [CH] Switzerland ............. 10883/71

[51] Int. Cl.³ ..................... A01N 57/00
[52] U.S. Cl. ................ 424/225; 260/964
[58] Field of Search ............ 260/964; 424/225

[56] References Cited

U.S. PATENT DOCUMENTS 3,839,511  10/1974  Kishino et al. ............ 260/964

FOREIGN PATENT DOCUMENTS 800230  1/1971  Switzerland ............. 260/964

*Primary Examiner*—Leonard Schenkman
*Attorney, Agent, or Firm*—Holman & Stern

[57] ABSTRACT

New thiophosphoric acid esters of the formula

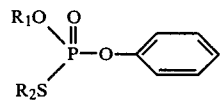

and their manufacture are disclosed; in this formula $R_1$ is methyl, ethyl, n-propyl or isopropyl and $R_2$ is n-propyl or isopropyl. Such compounds are suitable as active ingredients for combating nematodes.

2 Claims, No Drawings

NEMATOCIDAL UNSUBSTITUTED PHENYL ESTERS OF O-ALKYL-S-ALKYL-THIOPHOSPHORIC ACID

This is a continuation of application Ser. No. 746,689, filed Dec. 2, 1976, which in turn is a continuation of Ser. No. 652,865, filed Jan. 27, 1976, which in turn is a Rule 60 Divisional of Ser. No. 445,011, filed Feb. 22, 1974, which is a cont. Ser. No. 273,075, July 19, 1972 all of which are now abandoned.

The present invention relates to new thiophosphoric acid esters, to processes for their production, to nematocidal agents containing these new esters as active substances, as well as to processes for the control of nematodes by application of the new esters or of agents containing them.

The new thiophosphoric acid esters correspond to the formula

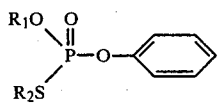
(I)

wherein
$R_1$ stands for methyl, ethyl, n-propyl or isopropyl, and
$R_2$ stands for n-propyl or i-propyl.

The new thiophosphoric acid esters of formula I are produced according to the present invention, with application of processes known per se, by the conversion of a phosphonic acid halide of the formula

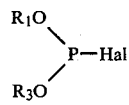
(II)

with a sulphenic acid halide of the formula

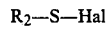
(III), in the presence of a solvent or diluent inert to the reactants, into thiophosphoric acid halides of the formula

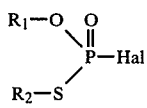
(IV);

and subsequently the reaction of these with phenol in the presence of an acid-binding agent (proton acceptor) and of a solvent or diluent inert to the reactants. The symbols $R_1$ and $R_2$ in the formulae II to IV have the meanings given under formula I, $R_3$ stands for methyl, ethyl, n-propyl, isopropyl, and Hal represents chlorine or bromine, preferably chlorine.

It has been shown in the carrying out of the process according to the invention that the yields and the purity of the intermediates of formula IV are raised if, instead of a sulphenic acid halide of formula III, the corresponding alkyldisulphides [$(R_2S)_2$] and sulphuryl halide are used. The corresponding sulphenic acid halide is then formed in situ as the reaction occurs.

By use of this process, developed by A. E. Lipmann, J.org.Chem. 30, 3217 (1965), the thiophosphoric acid halides of formula IV are obtained with an excellent level of yield (95%) and of purity. They can be employed direct for the reaction with phenol. For this stage of the process, the reaction temperature are in the range of $-20°$ to $+20°$ C., preferably between $-20°$ and $0°$ C. Sulphenic acid halides of formula II can be obtained according to Houben Weyl, Vol. 9, p. 272 onwards, by the reaction of mercaptans with N-halogenosuccinimides or halogen, e.g. with liquid chlorine. The thiophosphoric acid halides of formula IV can also be obtained by reaction of phosphorus oxychloride with an equivalent of an alkanol or its salts and with an equivalent of an alkali mercaptide (cp. Houben Weyl, Vol. 12/2, p. 213 onwards). The thiophosphoric acid halides of formula IV have not been hitherto described and are, therefore, new compounds.

The reaction of thiophosphoric acid halides of formula IV with phenol is performed at temperatures of between $0°$ and $+50°$ C., preferably between $10°$ and $30°$ C. The use of an acid-binding agent is necessary for this step of the process. Organic bases are particularly suitable, such as trialkylamines, e.g. triethylamine, pyridine and pyridine bases, quaternary ammonium bases; also inorganic bases such as the carbonates and hydrocarbonates of alkali metals and alkaline earth metals, also alkali metal hydroxides and alkaline earth metal hydroxides.

The following solvents and diluents inert to the reactants are suitable for the process according to the invention: aliphatic, aromatic or halogenated hydrocarbons such as benzene, toluene, xylenes, chlorobenzene, chloroform, methylene chloride, ethylene chloride; ethers and ethereal compounds such as dialkyl ether, dioxane, tetrahydrofuran; ketones such as acetone, methyl ethyl ketone; nitriles such as acetonitrile; N,N-dialkylated amides such as dimethylformamide; dimethylsulphoxide, as well as mixtures of these solvents.

For the first stage of the process, aliphatic and aromatic hydrocarbons, especially toluene and xylenes, are preferred as solvents, and for the second stage ethers, particularly dialkyl ether.

Furthermore, it has proved advantageous, with regard to purity and yield of the products obtained by the process, for the two stages to be performed in an inert gas atmosphere; nitrogen gas is most suitable for the purpose.

Although equimolar proportions of the reactants are suitable and generally preferred, it is also possible to use large or small excesses of the reactants according to the invention, without impairment of the reactions. As always, however, an extremely large excess is impracticable.

The new thiophosphoric acid esters of formula I can moreover be obtained by the conversion of an O,O-dialkyl-O-phenylthiophosphate with an alkali hydrosulphide into the corresponding salt; and the subsequent reaction of this with an alkyl halide (cp. French Pat. No. 1,567,444).

Such compounds which act by way of the gas phase, such as, e.g., 1,2-dibromo-3-chloropropene and mixtures of dichloropropane and dichloropropene, or which undergo in the soil rapid decomposition, such as, e.g. the sodium salt of monomethyldithiocarbamic acid or 3,5-dimethyltetrahydro-1,3,5-thiadiazine-2-thione, have hitherto assumed importance as nematocidal active substances. The mentioned salt of monomethyldithiocarbamic acid, however, is storage-stable only as solution of a specific concentration, and only as such does it possess the required stability; so that consequently the very desired forms of application, e.g. as a granulate or as a scattering agent, have to be excluded. The smell nuisance (dithiocarbamates) occurring after application of the mentioned nematocides, and the irritant effect of halogenated alkanes and alkenes, limit the field of application of such compounds to an enormous extent. In practical application concentrations, the thiadiazine derivative has an inadequate effect.

The employment of certain phosphoric acid esters for the control of nematodes is known. One of the disadvantages of the phosphorus compounds suggested as nematocides was the necessity of using them in relatively high concentrations. Since mostly very toxic compounds are involved, there are considerable limitations with regard to their applicability.

In the French Pat. No. 1,567,444, O,S-dialkyl-O-phenylthiophosphoric acid esters, amongst other compounds, are described as fungicidal and insecticidal active substances. The O-ethyl-S-n-butyl- and S-sec.butyl-O-phenylthiophosphoric acid esters mentioned there do not have, in practical application concentrations, a satisfactory nematocidal action.

It was therefore not to be anticipated that the active substances of formula I according to the invention are excellently suitable for the control of nematodes, and have no disadvantages such as smell nuisance, irritant effect, high toxicity towards warm-blooded animals, instability in storage, etc.

Of the thiophosphorus esters of formula I, the O-ethyl-S-n-propyl- and -S-isopropyl-O-phenylthiophosphoric acid esters are of particular value. These compounds are effective against soil nematodes and against stem and leaf nematodes, and have moreover a systemic action.

The thiophosphoric acid esters of formula I according to the invention are suitable for the control of phytopathogenic nematodes such as, e.g. Meloidogyne spp., Heterodera spp., Ditylenchus spp., Pratylenchus spp., Paratylenchus spp., Anguina spp., Helicotylenchus spp., Tylenchorhynchus spp., Rotylenchulus spp., *Tylenchulus semipenetrans, Radopholus similis,* Belonolaimus spp., Trichodorus spp., Longidorus spp., Aphelenchoides spp., Xiphinema spp. and Rhadinaphelenchus spp.

The following tests serve to illustrate the nematocidal action of the new thiophosphoric acid esters.

The new active substances are used in the form of solid or liquid agents for the control of nematodes. For application to the soil, such agents are particularly advantageous which ensure a uniform distribution of the active substances through a layer of soil extending to a depth of 15 to 25 cm. The mode of application and the form of preparation depend, in particular, on the specie of nematodes to be controlled, on the climate and on the conditions of the soil. Since the new active substances are not phytotoxic and do not impair germination power, they may be applied, without the observance of a waiting period directly before or after the sowing of the plants. It is likewise possible to treat already established crops with the new agents.

Furthermore, for promotion of propagation, certain parts of plants, such as seed, sections of stems (sugar cane) or bulbs, as well as roots or seedlings, can be dipped into dispersions or solutions of the active substances according to the invention, or dressed with these active substances.

The agents according to the invention are produced in a manner known per se by the intimate mixing and grinding of active substances of the general formula I with suitable carriers, optionally with the addition of dispersing agents or solvents which are inert to the active substances. The active substances can be obtained and used in the following forms:

solid preparations: dusts, scattering agents, granulates, (coated granulates, impregnated granulates and homogeneous granulates):

water-dispersible concentrates of the active substance: wettable powders, pastes, emulsions;

liquid preparations: solutions.

The solid preparations (dusts, scattering agents, granulates) are produced by the mixing of the active substances with solid carriers. Suitable carriers are, e.g. kaolin, talcum, bole, loess, chalk, limestone, ground limestone, Attaclay, dolomite, diatomaceous earth, precipitated silicic acid, alkaline-earth silicates, sodium and potassium aluminium silicates (feldspar and mica), calcium and magnesium sulphates, magnesium oxide, ground synthetic materials, fertilisers such as ammonium sulphate, ammonium phosphate, ammonium nitrate, urea, ground vegetable products such as bran, bark dust, sawdust, ground nutshells, cellulose powder, residues of plant extractions, active charcoal, etc., alone or in admixture with each other.

The particle size of the carriers is for dusts advantageously up to about 0.1 mm; for scattering agents from about 0.075 mm to 0.2 mm; and for granulates 0.2 mm or coarser.

The concentrations of active substance in the solid preparation forms are from 0.5 to 80%.

To these mixtures may also be added additives stabilising the active substance, and/or non-ionic, anion-active, and cation-active substances, which, for example, improve the adhesiveness of the active substances on plants and on parts of plants (adhesives and agglutinants), and/or ensure a better wettability (wetting agents) and dispersibility (dispersing agents). Suitable adhesives are, for example, the following: olein/chalk mixture, cellulose derivatives (methyl cellulose, carboxymethyl cellulose), hydroxyethylene glycol ethers of monoalkyl and dialkyl phenols having 5 to 15 ethylene oxide radicals per molecule and 8 to 9 carbon atoms in the alkyl radical, ligninsulphonic acid, its alkali metal and alkaline-earth metal salts, polyethylene glycol ethers (carbowaxes), fatty alcohol polyethylene glycol ethers having 5 to 20 ethylene oxide radicals per molecule and 8 to 18 carbon atoms in the fatty alcohol moiety, condensation products of ethylene oxide, propylene oxide, polyvinyl pyrrolidones, polyvinyl alcohols, condensation products of urea and formaldehyde, as well as latex products.

Water-dispersible concentrates of active substance, i.e. wettable powders, pastes and emulsion concentrates, are agents which can be diluted with water to obtain any desired concentration. They consist of active substance, carrier, optionally additives which stabilise the active substance, surface-active substances, and anti-foam agents and, optionally, solvents. The concentration of active substance in these agents is 5 to 80%.

The wettable powders and the pastes are obtained by the mixing and grinding of the active substances with dispersing agents and pulverulent carriers, in suitable devices, until homogeneity is attained. Suitable carriers are, e.g. those previously mentioned in the case of solid preparations. It is advantageous in some cases to use mixtures of different carriers. As dispersing agents it is possible to use, e.g.: condensation products of sulphonated naphthalene and sulphonated naphthalene derivatives with formaldehyde, condensation products of naphthalene or of naphthalenesulphonic acids with phenol and formaldehyde, as well as alkali, ammonium and alkaline-earth metal salts of ligninsulphonic acid, also alkylaryl sulphonates, alkali metal salts and alkaline-earth metal salts of dibutyl naphthalenesulphonic acid, fatty alcohol sulphates such as salts of sulphated hexadecanols, heptadecanols, octadecanols, and salts of sulphated fatty alcohol glycol ether, the sodium salt of oleyl methyl tauride, ditertiary aceteylene glycols, dialkyl dilauryl ammonium chloride, and fatty acid alkalimetal and alkaline-earth metal salts.

Suitable anti-foam agents are, for example, silicones.

The active substances are so mixed, ground, sieved and strained with the above mentioned additives that the solid constituent in the case of wettable powders has a particle size not exceeding 0.02 to 0.04 mm, and in the case of pastes not exceeding 0.03 mm. Dispersing agents such as those mentioned in the preceding paragraphs, organic solvents and water are used in the preparation of emulsion concentrates and pastes. Suitable solvents are, e.g. the following: alcohols, benzene, xylenes, toluene, dimethylsulphoxide, and mineral oil fractions boiling in the range of 120° to 350° C. The solvents must be practically odourless, nonphytotoxic, inert to the active substances, and not readily inflammable.

The agents according to the invention may also be employed in the form of solutions. For this purpose the active substance (or several active substances) of the general formula I is (or are) dissolved in suitable organic solvents, solvent mixtures, or water. As organic solvents it is possible to use aliphatic and aromatic hydrocarbons, their chlorinated derivatives, alkylnaphthalenes, mineral oils on their own or in admixture with each other. The solutions should contain the active substance in a concentration of from 1 to 20%.

Other biocidal active substances or agents may be added to the described agents according to the invention. For the widening of their sphere of action, the new agents may contain, in addition to the stated compounds of the general formula I, e.g. insecticides, fungicides, bactericides, fungistatics, bacteriostatics or nematocides. The agents according to the invention can also contain fertilisers, trace elements, etc.

Preparations of the new active substances of the general formula I are described in the following. The term 'parts' denotes parts by weight.

WETTABLE POWDER

The following constituents are used for the preparation of (a) a 50%, (b) a 40%, (c) a 25%, and (d) a 10% wettable powder:

(a)

50 parts of active substance,
5 parts of naphthalenesulphonic acid/benzenesulphonic acid/formaldehyde condensate,
5 parts of dibutylnaphthalenesulphonic acid,
5 parts of Champagne chalk,
30 parts of silicic acid,
5 parts of kaolin;

(b)

40 parts of active substance,
1 part of dibutylnaphthalenesulphonic acid,
5 parts of sodium lignin sulphonate,
2 parts of a 1:1 mixture of Champagne chalk and hydroxyethylcellulose,
27 parts of kaolin,
25 parts of sodium aluminium silicate;

(c)

25 parts of active substance,
5 parts of the sodium salt of oleyl methyl tauride,
2.5 parts of naphthalenesulphonic acid/formaldehyde condensate,
0.5 part of carboxymethylcellulose,
5 parts of neutral potassium aluminium silicate,
65 parts of talcum;

(d)

10 parts of active substance,
1 part of sodium dibutyl naphthalene sulphonate,
4 parts of the sodium salt of ligninsulphonic acids,
2 parts of hydroxymethylcellulose,
10 parts of sodium aluminium silicate,
23 parts of Champagne chalk,
50 parts of kaolin.

The active substances are intimately mixed, in suitable mixers, with the additives, and ground in the appropriate grinding mills and rollers. Wettable powders are obtained which can be diluted with water to obtain suspensions of any desired concentration.

DUSTING AGENT

The following substances are used for the preparation of (a) a 10%, (b) a 5%, and (c) a 2% dusting agent:

(a)

10 parts of active substance,
5 parts of highly dispersed silicic acid,
85 parts of talcum;

(b)

5 parts of active substance,
95 parts of talcum;

(c)

2 parts of active substance,
1 part of highly dispersed silicic acid,
97 parts of talcum.

The active substances are mixed and ground with the carriers.

EMULSION CONCENTRATE

The following constituents are mixed together for the preparation of a 25% emulsion concentrate:

25 parts of active substance,
5 parts of a mixture of nonylphenolpolyoxyethylene and calcium dodecylbenzenesulphonate ("Emullat P 140 HFP"),
35 parts of isophorone (3,5,5-trimethyl-2-cyclohexen-1-one)
25 parts of dimethylformamide.

This concentrate can be diluted with water to obtain emulsions of suitable concentration.

GRANULATE

The following substances are used for the preparation of a 5% and of a 10% granulate:

(a)

5 parts of active substance,
0.25 part of epichlorohydrin,
0.25 part of cetyl polyglycol ether,
3.50 parts of polyethylene glycol ("carbowax"),
91 parts of kaolin (particle size 0.3 to 0.8 mm);

(b)

10 parts of active substance,
10 parts (flash point 50°-54° C.)
2 parts of polyethylene glycol ("carbowax 400"),
1 part of silicic acid,
77 parts of ground limestone (0.4 to 0.8 mm).

The active substances are mixed with epichlorohydrin or with paraffin, and dissolved with 6 parts of acetone; additions are then made of polyethylene glycol and cetyl polyglycol ether. The thus obtained solutions are absorbed on to kaolin or ground limestone, and the acetone is subsequently evaporated off in vacuo.

EXAMPLE 1

(a) An amount of 89 g of sulphuryl chloride in 200 ml of toluene is added dropwise at −10° C. in a nitrogen atmosphere, whilst stirring is maintained, to a solution of 99.2 g of di-n-propyldisulphide in 200 ml of toluene. An addition is then made dropwise to this mixture at −10° C., with stirring and in an $N_2$-atmosphere, of 206.5 g of diethylphosphonic acid chloride in 400 ml of toluene. The reaction mixture is subsequently stirred for 2 hours at −10° C. under an $N_2$-atmosphere. The mixture is afterwards allowed to stand at room temperature for 2 hours, and the toluene then distilled off in vacuo (14 Torr and 50°-60° C. water bath). The obtained O-ethyl-S-n-propyl-thiophosphoric acid ester chloride has the refractive index $n_D^{23°}$: 1.4788, (yield 240 g=98.8% of theory) B.P. 58° C., 12 Torr.

There is obtained in an analogous manner, with the use of 150.3 g of diisopropyl-disulphide, 134.9 g of sulphuryl chloride and 313.5 g of O,O-diethylphosphonic acid chloride, an amount of 319 g of O-ethyl-S-isopropyl-thiophosphoric acid chloride having the refractive index $n_D^{20°}$: 1.4794.

(b) An amount of 19.3 g of O-ethyl-S-n-propyl-thiophosphoric acid chloride dissolved in 30 ml of diethyl ether is added dropwise at 20° to 25° C., in a nitrogen atmosphere, to a solution of 6.0 g of phenol and 6.5 g of triethylamine in 70 ml of diethyl ether (anhydrous). The mixture is then stirred for one hour at room temperature. The precipitated triethylamine chlorohydrate is separated; the filtrate is washed with 0.1 N hydrochloric acid water, 0.1 N sodium hydroxide solution and then again with water, and afterwards dried. The solvent is removed and the residue distilled in vacuo. The obtained O-ethyl-S-n-propyl-O-phenyl-thiophosphoric acid ester has the boiling point: 105°-107° C. under 0.012 Torr.

There is obtained in an analogous manner, with the use of 9.4 g of phenol, 10.1 g of triethylamine and 20.2 g of O-ethyl-S-isopropyl-thiophosphoric acid chloride, an amount of 16.8 g of O-ethyl-S-isopropyl-O-phenyl-thiophosphoric acid ester, B.P. 104°-107° C. at $10^{-4}$ Torr. The following compounds are also obtained analogously:

O-methyl-S-n-propyl-O-phenyl-thiophosphoric acid ester,
O-methyl-S-isopropyl-O-phenyl-thiophosphoric acid ester,
O,S-di-n-propyl-O-phenyl-thiophosphoric acid ester,
O-n-propyl-S-isopropyl-O-phenyl-thiophosphoric acid ester,
O-isopropyl-S-n-propyl-O-phenyl-thiophosphoric acid ester,
O,S-di-iso-propyl-O-phenyl-thiophosphoric acid ester.

EXAMPLE 2

NEMATOCIDAL TEST

In order to test the action against soil nematodes, the active substance is added, in the stated concentration, to soil infested by root-gall nematodes (*Meloidogyne arenaria*), and the whole intimately mixed. In the test series A (Table 1), tomato seedlings are planted immediately afterwards in the thus prepared soil; and in the test series B (Table 2), tomatoes are sown therein after a waiting period of 8 days.

For an assessment of the nematocidal action, the galls present on the roots are counted 28 days after planting and sowing, respectively.

Evaluation: 0 = complete nematocidal action, no infestation;
3 = no nematocidal action: the same degree of infestation as in the control test;
1 and 2 = intermediate stages of infestation.

TABLE 1

Test series A
Concentration: 50 ppm*

| Active substance: | Nematocidal action |
|---|---|
| O-ethyl-S-n-propyl-O-phenylthiophosphoric acid ester, | 0 |
| O-ethyl-S-isopropyl-O-phenylthiophosphoric acid ester, | 0 |
| O,O-diethyl-O-phenylphosphoric acid ester (known), | 2 |
| O,O-diethyl-O-2,4-dichlorophenylthiophosphoric acid ester, (known from U.S. Pat. No. 2,761,806, under the trade-name of "VC-13-Nemacide" of the Virginia-Carolina Chem. Corp.) | 3 |
| 3,5-dimethyl-2-thiotetrahydro-2H-1,3,5-thiadiazine, (known under the trade-name of "Dazomet") | 3 |

*X ppm = X parts of active substance in $10^6$ parts of soil.

TABLE 1

Test series B
Concentration: 50 ppm*

| Active substance | Nematocidal action |
|---|---|
| O-ethyl-S-n-propyl-O-phenyl-thiophosphoric acid ester, | 0 |
| O-ethyl-S-isopropyl-O-phenyl-thiophosphoric acid ester, | 0 |
| O,O-diethyl-O-phenylphosphoric acid ester (known), | 2 |
| O,O-diethyl-0,2,4-dichlorophenyl-thiophosphoric acid ester, (known from U.S. Patent No. 2,761,806 under the trade-name of "VC-13-Nemacide" of the Virginia-Carolina Chem. Corp.) | 3 |
| 3,5-dimethyl-2-thiotetrahydro-2H-1,3,5-thiadiazine, (known under the trade-name of "Dazomet") | 2 |

*X ppm = X parts of active substance in $10^6$ parts of soil.

We claim:
1. A nematocidal composition comprising a nematocidally effective amount of O-ethyl-S-n-propyl-O-phenylthiophosphate in admixture with a diluent.
2. A method of controlling nematodes which comprises applying to said nematodes a nematocidally effective amount of O-ethyl-S-n-propyl-O-phenyl-thiophosphate.

* * * * *